US00PP27984P3

(12) United States Plant Patent
Semkow

(10) Patent No.: US PP27,984 P3
(45) Date of Patent: May 9, 2017

(54) ARBORVITAE PLANT NAMED 'SPIREANDELA'

(50) Latin Name: *Thuja occidentalis*
Varietal Denomination: Spireandela

(71) Applicant: Franklin D. Semkow, Litchfield, OH (US)

(72) Inventor: Franklin D. Semkow, Litchfield, OH (US)

( * ) Notice: Subject to any disclaimer, the term of this patent is extended or adjusted under 35 U.S.C. 154(b) by 163 days.

(21) Appl. No.: 14/544,459

(22) Filed: Jan. 9, 2015

(65) Prior Publication Data

US 2016/0205845 P1 Jul. 14, 2016

(51) Int. Cl.
*A01H 7/00* (2006.01)

(52) U.S. Cl.
USPC ..... Plt./213

(58) Field of Classification Search
USPC ..... Plt./213
See application file for complete search history.

*Primary Examiner* — June Hwu

(57) ABSTRACT

A new and distinct variety of *Thuja* plant (commonly known as arborvitae) named 'Spireandela' characterized by very dense curved foliage arranged in a loose upward spiral, very narrow columnar shape, and slow growth habit. It can be grown as a narrow hedging or specimen plant.

2 Drawing Sheets

BACKGROUND OF THE INVENTION

The present invention relates to a new and distinct variety of cultivar of *Thuja occidentalis* (commonly known as arborvitae) plant that is slow growing for the species, very narrow columnar shape and distinctly different from any other *Thuja occidentalis* plant known to the inventor in that the dense foliage is curved and that curved foliage is arranged in a loose upward spiral forming the tree. The new variety was discovered as a naturally occurring chance seedling in about the year 1980, growing in a bed of *Thuja*, an unpatented variety in a nursery cultivated on my property located at 4532 Beat Rd., Litchfield, Medina County, Ohio. The original plant was a single chance seedling which came from a group of 500 bare root *Thuja* seedlings obtained in 1976. The parent plants are unknown, the probable parent plants are *Thuja occidentalis*, Asexual reproduction by hardwood branch cuttings in Litchfield, Ohio by me since the year 2002 of the new and distinct variety has produced descendants that exhibit that the foregoing characteristics come true to form and are established and transmitted thru succeeding propagations.

BRIEF SUMMARY OF THE INVENTION

Although similar in height to 'Emerald' (aka 'Smaragd'), an unpatented variety, it differs in that the new variety has foliage assembled into slightly concave, fan shaped sprays principally orientated in a horizontal plane in layers of foliage arranged in a loose upward spiral while 'Emerald' (aka 'Smaradg') has foliage with flat sprays arranged in a more or less vertical plane. While this new variety resembles the patented variety 'American Pillar', (U.S. Plant Pat. No. 20,209) it differs in that the new variety is very slow growing being 3.8 meters (12.5 feet) tall and 71 centimeters (28 inches) diameter at 24 years while 'American Pillar' shows fast growth to about 7 meters (22.9 feet) tall and 1 meter (3.3 feet) diameter after 6 growing seasons. The new variety differs in that is a chance seedling while 'American Pillar' is a branch mutation sport of 'Hetz Wintergreen'. It differs from the other *Thuja occidentalis* in the planting which measure about 6 to 7.5 meters tall (19.7 to 24.6 feet) and 3 meters (10 feet) diameter at 24 years. The new variety has a dense foliage, it differs in that sprays are curved in 3 dimensions while sprays of typical *Thuja occidentalis* sprays are flat in one plane. The new variety also differs in that it has approximately twice the foliage density of about 1334 sprays per square meter (124 sprays per square foot), with foliage arranged in a loose upward spiral, compared to the typical *Thuja occidentalis* in the planting, resulting in a plant of particular beauty, The new variety is particularly suited for planting in places where slow growth is desired such as cemeteries, areas with limited planting space or as a specimen plant.

BRIEF DESCRIPTION OF ILLUSTRATION

The accompanying photographs illustrate the present invention as follows:

FIG. 1 is a printout of a digital photograph showing the shape and size of *Thuja occidentalis* 'Spireandela' at 24 years of age. The markings on the surveyors pole are 30.5 centimeters (1 foot) apart.

FIG. 2 is a printout of a digital photograph showing the detail of the curved foliage looking down on a rooted cutting.

BOTANICAL DESCRIPTION

The following observations, measurements and values describe plants grown in my outdoor nursery located at 4532 Beat Rd. Litchfield, Ohio.

Below is a detailed description of *Thuja* cultivar 'Spireandela'. The color terminology is from The Royal Horticultural Society (R.H.S.) Colour Charts 1986. Data was collected from a container grown plant in Litchfield, Ohio. Growing requirements are similar to the species.

Botanical classification: *Thuja occidentalis* cultivar 'Spireandela'.

Growth habit: Dense, uniform narrow upright.

Shape: Narrow columnar.

Parentage: Chance seedling of *Thuja occidentalis*.

Propagation: Hardwood branch cuttings.

Root description: Creamy white RHS 156A in growing points at ends of roots, light brown RHS 199D elsewhere.

Rooting habit: Freely branching, long dense.

Form: Narrow columnar form. Sides tapered to vertical trunk about 2-½ degrees per side.

Branching habit: The branches organized in spiral arrangement along the vertical main stem, ascent at an angle of 30-45 degrees from vertical.

Plant height: (At 24 years) about 3.8 meters (12.5 feet).

Plant diameter: (At 24 years) about 71 centimeters (28 inches).

Main trunk diameter: About 7 centimeters (2.7 inches) at 0.9 meter (3 feet) above ground level. Single or multiple trunk.

Trunk: Bark fissured, with shallow furrows and vertical shedding strips, color: RHS 200B.

Branch length: About 0.5 meter (20 inches).

Branch diameter: 1 centimeter (0.39 inch).

Branch color: Coming close to RHS 200D.

Foliage habit: The foliage is assembled into slightly concave, fan-shaped sprays principally orientated in a horizontal plane at the same angle as the branches. The tips of the sprays are lax, arching over so that they are horizontal to slightly pendant. The effect produced that of overlapping layers of foliage arranged in a loose upward spiral is similar to cultivars of the Hinoki falsecypress, *Chamaecyparis obtusa*, but is not displayed by any cultivar of *Thuja occidentalis* with which I am familiar. Foliage tight, dense; density approximately double greater than density typical of *Thuja occidentalis*, approximate 1334 sprays per square meter (124 sprays per square foot).

Leaves: Scale like, rhombic, oviate, acute, about 1 millimeter long, 0.5 millimeter wide closely appressed coming close to being imbricated. Typical of *Thuja occidentalis*. Born on curved sprays and flat shoots.

Leaf color: Summer coloration, upper surface coming close to RHS 134A, lower surface coming close to RHS 138B.

Winter coloration: With the onset of cold weather the upper surface color coming close to RHS 137B, lower surface close to RHS 137D. Difference in color between darker upper side and lighter lower side of leaf typical of *Thuja occidentalis*. Growing leaf tips are close to RHS 134B.

Odor: Leaves emitting a cedar like odor when bruised.

Hardiness: Observation of the parent growing in Litchfield, Ohio has been observed go be tolerant to drought, rain, wind and temperatures from −23.3 degrees C. (−10 degrees F.) to 38.9 degrees C. (102 degrees F.) growing in USDA hardiness zone 6A (formerly zone 5) for 35 seasons. Full sun or partial shade.

Vigor: The growth rate is less than the species.

Cones: Monoecius, characteristic of the species.

Male cones: Terminal on small branchlets, solitary, color RHS 200D when mature.

Female cones: Clustered, 9 to 11 millimeters long, 4 millimeters in diameter, color RHS 200D when mature.

Glands: Raised glands just below the tip of some leaves, but not all leaves, observed on one or both sides of branchlets.

Disease and insect resistance: No particular resistance or susceptibility has been observed.

The invention claimed is:

1. A new and distinct variety of *Thuja* plant named 'Spireandela' substantially as illustrated and described herein.

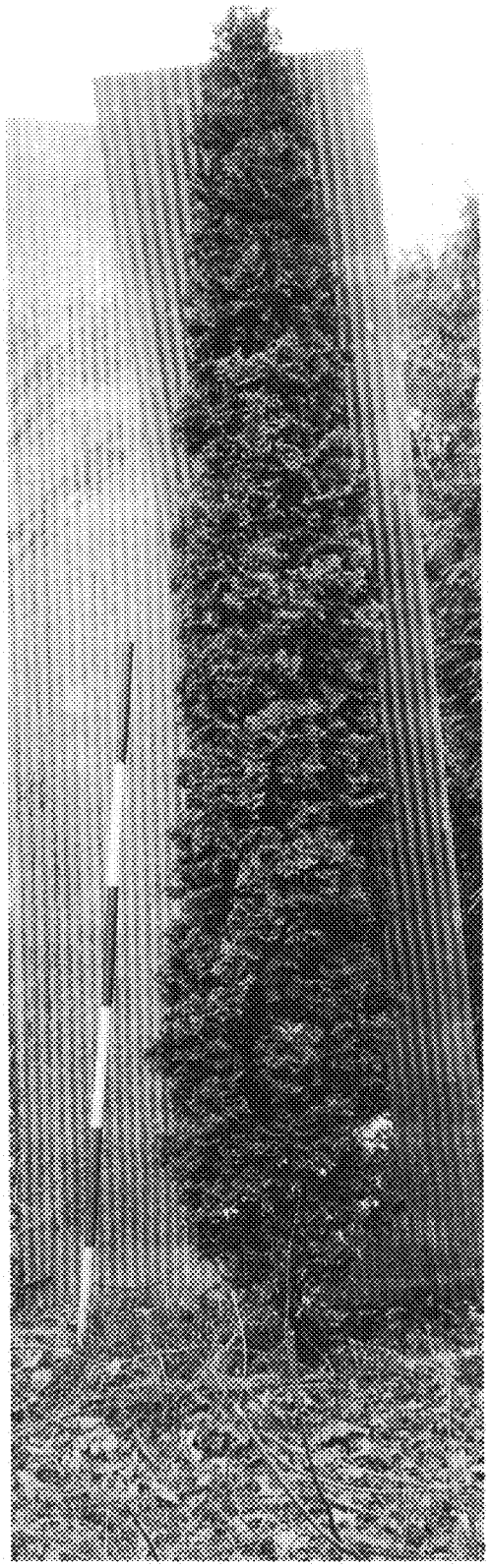

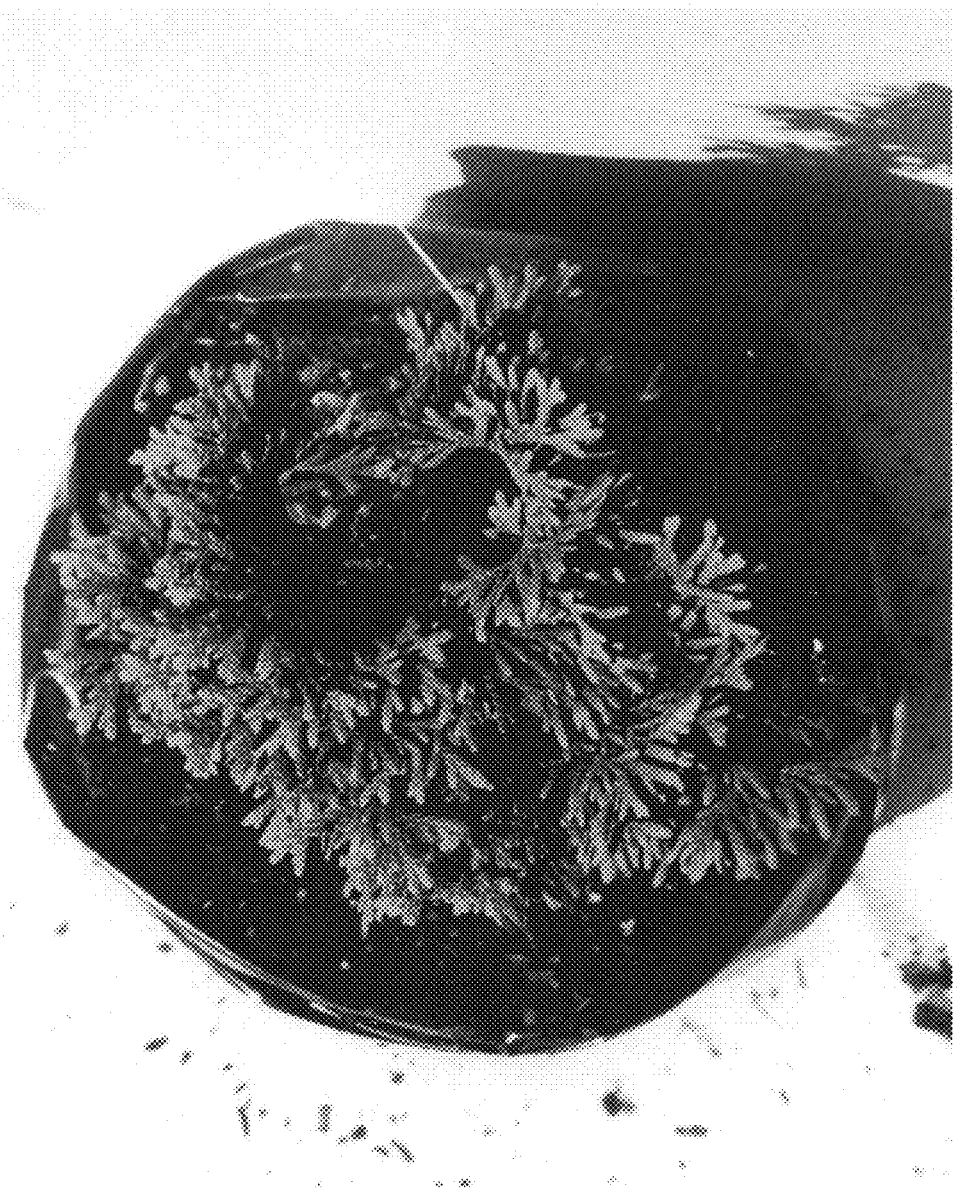

* * * * *